United States Patent
Ohta et al.

(10) Patent No.: US 9,907,532 B2
(45) Date of Patent: Mar. 6, 2018

(54) ULTRASOUND INSPECTION APPARATUS, SIGNAL PROCESSING METHOD FOR ULTRASOUND INSPECTION APPARATUS, AND RECORDING MEDIUM

(71) Applicant: FUJIFILM Corporation, Tokyo (JP)

(72) Inventors: Yasunori Ohta, Ashigara-kami-gun (JP); Tsuyoshi Tanabe, Ashigara-kami-gun (JP); Noriaki Ida, Ashigara-kami-gun (JP); Shin Nakata, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1091 days.

(21) Appl. No.: 14/140,368

(22) Filed: Dec. 24, 2013

(65) Prior Publication Data

US 2014/0187938 A1 Jul. 3, 2014

(30) Foreign Application Priority Data

Dec. 27, 2012 (JP) .................. 2012-284106

(51) Int. Cl.
*A61B 8/00* (2006.01)
*A61B 8/08* (2006.01)

(52) U.S. Cl.
CPC .............. *A61B 8/08* (2013.01); *A61B 8/5207* (2013.01); *A61B 8/5269* (2013.01); *A61B 8/5292* (2013.01); *A61B 8/54* (2013.01); *A61B 8/4494* (2013.01)

(58) Field of Classification Search
CPC ........................... A61B 8/5207; A61B 8/5292
See application file for complete search history.

(56) References Cited

U.S. PATENT DOCUMENTS

| 6,221,020 B1 * | 4/2001 | Lysyansky | A61B 8/06 600/453 |
| 8,372,008 B2 | 2/2013 | Katsuyama | |
| 2010/0076312 A1 * | 3/2010 | Katsuyama | A61B 8/00 600/443 |

FOREIGN PATENT DOCUMENTS

| JP | 2006-325955 A | 12/2006 |
| JP | 2010-99452 A | 5/2010 |

\* cited by examiner

*Primary Examiner* — Rajeev Siripurapu
(74) *Attorney, Agent, or Firm* — Birch, Stewart, Kolasch & Birch, LLP (57) ABSTRACT

Provided is an ultrasound inspection apparatus ensuring the real-time property during ultrasound imaging, reducing the data amount to be stored, and making sound speed value correction after the imaging to allow improvement in image quality, tissue characterization, and so forth with high accuracy. The ultrasound inspection apparatus includes: a first reception signal memory storing element data; an image producer adapted to perform phasing and adding on element data based on a specified sound speed value to produce a sound ray signal, and produce ultrasound image data; a sound speed determiner adapted to determine the optimum sound speed value from a plurality of pieces of ultrasound image data produced using element data; a storage necessity determiner adapted to determine element data whether or not to satisfy a specified condition; and a second reception signal memory storing the element data as determined to satisfy the specified condition.

13 Claims, 5 Drawing Sheets

ULTRASOUND INSPECTION APPARATUS, SIGNAL PROCESSING METHOD FOR ULTRASOUND INSPECTION APPARATUS, AND RECORDING MEDIUM

BACKGROUND OF THE INVENTION

The present invention relates to an ultrasound inspection apparatus which images an inspection object, such as an organ in a living body, through transmission and reception of an ultrasonic beam to produce an ultrasound image for inspection or diagnosis of the inspection object, a signal processing method for an ultrasound inspection apparatus, and a recording medium having a program recorded thereon.

An ultrasound inspection apparatus using an ultrasound image has hitherto been put into practical use in the field of medicine. In general, this type of ultrasound inspection apparatus has an ultrasound probe equipped with a transducer array and an apparatus body connected to the ultrasound probe. An ultrasonic beam is transmitted from the ultrasound probe toward a subject, an ultrasonic echo from the subject is received by the ultrasound probe, and a reception signal corresponding to the reception of the ultrasonic echo is electrically processed by the apparatus body to produce an ultrasound image.

In the ultrasound inspection apparatus, when producing an ultrasound image, a reception signal (element data) received from each transducer of the ultrasound probe is subjected to delay time correction and signal synthesis (phasing and adding) to produce a sound ray signal, on the assumption that a sound speed in a living body of the subject is constant. Further, an ultrasound image is produced from the produced sound ray signal. However, there is variation in sound speed value in an actual living body, and due to the variation, spatial distortion arises in the ultrasound image.

Meanwhile, in recent years, in order to more accurately diagnose a region to be diagnosed in the subject, an imaging region is divided into a plurality of subregions, an appropriate sound speed value is measured for each subregion, and the distortion of image is corrected by producing an ultrasound image using the sound speed values measured (JP 2010-99452 A).

Moreover, it is conceived that, in the ultrasound inspection apparatus, data before producing an ultrasound image is stored, and after imaging for the ultrasound image ends, tissue characterization, improvement in image quality or the like is performed using the stored data.

For example, JP 2006-325955 A describes that RAW data which is data before scan conversion to image data is stored along with the image data, and after an ultrasound imaging ends, desired RAW data is searched for and used in order to obtain analysis data for diagnosis from such analyses as analysis for a speed image, analysis for a slope of speed change, distortion analysis, analysis for a displacement image, and the like.

The measurement of the sound speed value described in JP 2010-99452 A is performed at a predetermined timing, for example, for every several frames. If the measurement frequency is high, while the definition of the ultrasound image is improved, a required time for sound speed value calculation increases. For this reason, there is a problem in that real-time property of display of the ultrasound image is deteriorated. Moreover, in the measurement of the sound speed value, the more a region for measuring the sound speed value is segmentalized, the more the accuracy of correction is improved. Even in this case, however, a required time for sound speed value calculation increases, and accordingly, there is a problem in that real-time property is deteriorated.

Accordingly, as described in JP 2006-325955 A, it is thinkable to store data before image production so as to minimize the correction during ultrasound imaging and ensure the real-time property, and so as to perform detailed correction on the stored data or perform data analysis using the stored data after the ultrasound imaging ends.

However, the RAW data which is described in JP 2006-325955 A as data to be stored is data after phasing and adding the reception signal received from the ultrasound probe. For this reason, it is not possible to correct the sound speed value used in the phasing and adding of the reception signal, and to perform analysis for a sound speed value, distortion or the like with high accuracy.

If the reception signal (element data) before phasing and adding is stored, it is possible to perform correction of a sound speed value used in the phasing and adding of the reception signal or analysis for a sound speed value, distortion or the like with high accuracy. However, the amount of element data which is not subjected to processing such as phasing and adding is enormous. For this reason, in the conventional ultrasound inspection apparatus, element data received from the ultrasound probe is only stored temporarily, and the element data after being subjected to processing such as phasing and adding is sequentially deleted.

SUMMARY OF THE INVENTION

The present invention was accomplished in order to solve the above problems with the prior art, and an object thereof is to provide an ultrasound inspection apparatus, a signal processing method for an ultrasound inspection apparatus, and a recording medium capable of ensuring real-time property during ultrasound imaging, reducing the amount of data to be stored, performing correction of a sound speed value after the ultrasound imaging ends and thus improving image quality, and performing tissue characterization or the like with high accuracy.

In order to achieve the above-described objects, the present invention provides an ultrasound inspection apparatus which inspects an inspection object using an ultrasonic beam, the ultrasound inspection apparatus comprising: a transducer array having elements arranged therein that transmits the ultrasonic beam and receives an ultrasonic echo reflected by the inspection object to output an element signal according to the ultrasonic echo as received; a transmitter adapted to cause the transducer array to transmit the ultrasonic beam with the two or more elements serving as transmission apertures; a receptor adapted to perform specified processing on two or more element signals which are output from the transducer array having received ultrasonic echos with the two or more elements serving as reception apertures, so as to output resulting signals as one piece of element data; a first reception signal memory which stores a plurality of pieces of element data output from the receptor as a result of repeating ultrasonic transmission and reception through the transmitter and the receptor multiple times; an image producer adapted to perform phasing and adding individually on one or more pieces of element data based on a specified sound speed value to produce one or more sound ray signals, and produce ultrasound image data from the one or more sound ray signals; a sound speed determiner adapted to determine an optimum sound speed value from a plurality of pieces of ultrasound image data which are individually produced by the image producer based on a plurality of specified and set sound speeds and using one or more pieces of element data; a storage necessity determiner adapted to determine each piece of element data stored in the first reception signal memory whether or not to satisfy a specified condition; and a second reception signal memory which stores a piece of element data determined by the storage necessity determiner to satisfy the specified condition.

Preferably, the sound speed determiner determines the optimum sound speed value from a plurality of pieces of ultrasound image data which are individually produced by the image producer based on a plurality of specified and set sound speeds and using the one or more pieces of element data stored in the second reception signal memory; and the image producer produces ultrasound image data based on an initial sound speed value set in advance when producing ultrasound image data from the plurality of pieces of element data stored in the first reception signal memory, and produces ultrasound image data based on the optimum sound speed value calculated by the sound speed determiner when producing ultrasound image data from the one or more pieces of element data stored in the second reception signal memory.

Preferably, the second reception signal memory associates the piece of element data determined by the storage necessity determiner to satisfy the specified condition with a piece of ultrasound image data corresponding to the piece of element data so as to store them as such.

Further comprising an image memory which stores ultrasound image data produced by the image producer, wherein: the image memory stores ultrasound image data of all frames; and the second reception signal memory stores pieces of element data at specified frame intervals.

Further comprising a region-of-interest setter adapted to set a region of interest in an imaging region, wherein the storage necessity determiner determines a piece of element data corresponding to the region of interest to satisfy the specified condition.

Further comprising a region-of-interest setter adapted to set a region of interest in an imaging region, wherein, when an operation to set the region of interest has been detected, the storage necessity determiner determines pieces of element data corresponding to subsequent frames to satisfy the specified condition.

Further comprising a movement detector adapted to detect movement and standstill of a probe equipped with the transducer array, wherein, when the movement detector has detected standstill of the probe, the storage necessity determiner determines a piece of element data of a frame corresponding to the standstill of the probe to satisfy the specified condition.

Preferably, when a specified mode has been selected, the storage necessity determiner determines pieces of element data corresponding to subsequent frames to satisfy the specified condition.

Preferably, the storage necessity determiner determines a piece of element data which is obtained by transmitting an ultrasonic beam at a specified transmit frequency to satisfy the specified condition.

Preferably, the storage necessity determiner determines a piece of element data which is obtained by transmitting an ultrasonic beam having a specified amplitude to satisfy the specified condition.

Further comprising an image memory which stores ultrasound image data produced by the image producer, wherein: the sound speed determiner determines the optimum sound speed value from a plurality of pieces of ultrasound image data which are individually produced by the image producer based on a plurality of specified and set sound speeds and using the pieces of element data stored in the first reception signal memory; the image memory stores ultrasound image data of all frames; and the second reception signal memory stores pieces of element data at specified frame intervals, and stores the optimum sound speed value for a frame whose element data is not stored.

In order to achieve the above-described objects, the present invention also provides a signal processing method for an ultrasound inspection apparatus provided with a transducer array having elements arranged therein that transmits an ultrasonic beam and receives an ultrasonic echo reflected inside an inspection object to output an element signal according to the ultrasonic echo as received, which apparatus generates an ultrasonic beam by the transducer array to inspect the inspection object and produce ultrasound image data, the signal processing method comprising: a transmission step of causing the transducer array to transmit the ultrasonic beam with the two or more elements serving as transmission apertures; a reception step of performing specified processing on two or more element signals which are output from the transducer array having received ultrasonic echos with the two or more elements serving as reception apertures, so as to output resulting signals as one piece of element data; a first signal storage step of storing a plurality of pieces of element data output in the reception step as a result of repeating the transmission step and the reception step multiple times; an image production step of performing phasing and adding individually on one or more pieces of element data based on a specified sound speed value to produce one or more sound ray signals, and producing ultrasound image data from the one or more sound ray signals; a sound speed determination step of determining an optimum sound speed value from a plurality of pieces of ultrasound image data which are individually produced in the image production step based on a plurality of specified and set sound speeds and using one or more pieces of element data; a storage necessity determination step of determining each piece of element data stored in the first signal storage step whether or not to satisfy a specified condition; and a second signal storage step of storing a piece of element data determined in the storage necessity determination step to satisfy the specified condition. In order to achieve the above-described objects, the present invention also provides a computer-readable recording medium having a signal processing program for an ultrasound inspection apparatus recorded thereon, wherein the signal processing program causes a computer to execute a signal processing method for an ultrasound inspection apparatus provided with a transducer array having elements arranged therein that transmits an ultrasonic beam and receives an ultrasonic echo reflected inside an inspection object to output an element signal according to the ultrasonic echo as received, which apparatus generates an ultrasonic beam by the transducer array to inspect the inspection object and produce ultrasound image data, the signal processing method comprising: a transmission step of causing the transducer array to transmit the ultrasonic beam with the two or more elements serving as transmission apertures; a reception step of performing specified processing on two or more element signals which are output from the transducer array having received ultrasonic echos with the two or more elements serving as reception apertures, so as to output resulting signals as one piece of element data; a first signal storage step of storing a plurality of pieces of element data output in the reception step as a result of repeating the transmission step and the reception step multiple times; an image production step of performing phasing and adding individually on one or more pieces of element data based on a specified sound speed value to produce one or more sound ray signals, and producing ultrasound image data from the one or more sound ray signals; a sound speed determination step of determining an optimum sound speed value from a plurality of pieces of ultrasound image data which are individually produced in the image production step based on a plurality of specified and set sound speeds and using one or more pieces of element data; a storage necessity determination step of determining each piece of element data stored in the first signal storage step whether or not to satisfy a specified condition; and a second signal storage step of storing a piece of element data determined in the storage necessity determination step to satisfy the specified condition.

According to the invention, the necessity of storing element data is determined on the basis of a predetermined condition, and element data before phasing and adding which satisfies the predetermined condition is stored. Accordingly, it is possible to reduce the amount of data to be stored, to ensure real-time property during ultrasound imaging, to perform correction of a sound speed value or the like after the ultrasound imaging ends and thus to improve image quality, and to perform tissue characterization or the like with high accuracy.

DETAILED DESCRIPTION OF THE INVENTION

Hereinafter, an ultrasound inspection apparatus, a signal processing method for an ultrasound inspection apparatus, and a recording medium having a program recorded thereon according to the invention will be described in detail on the basis of the preferred embodiments as shown in the accompanying drawings.

Figure 1:
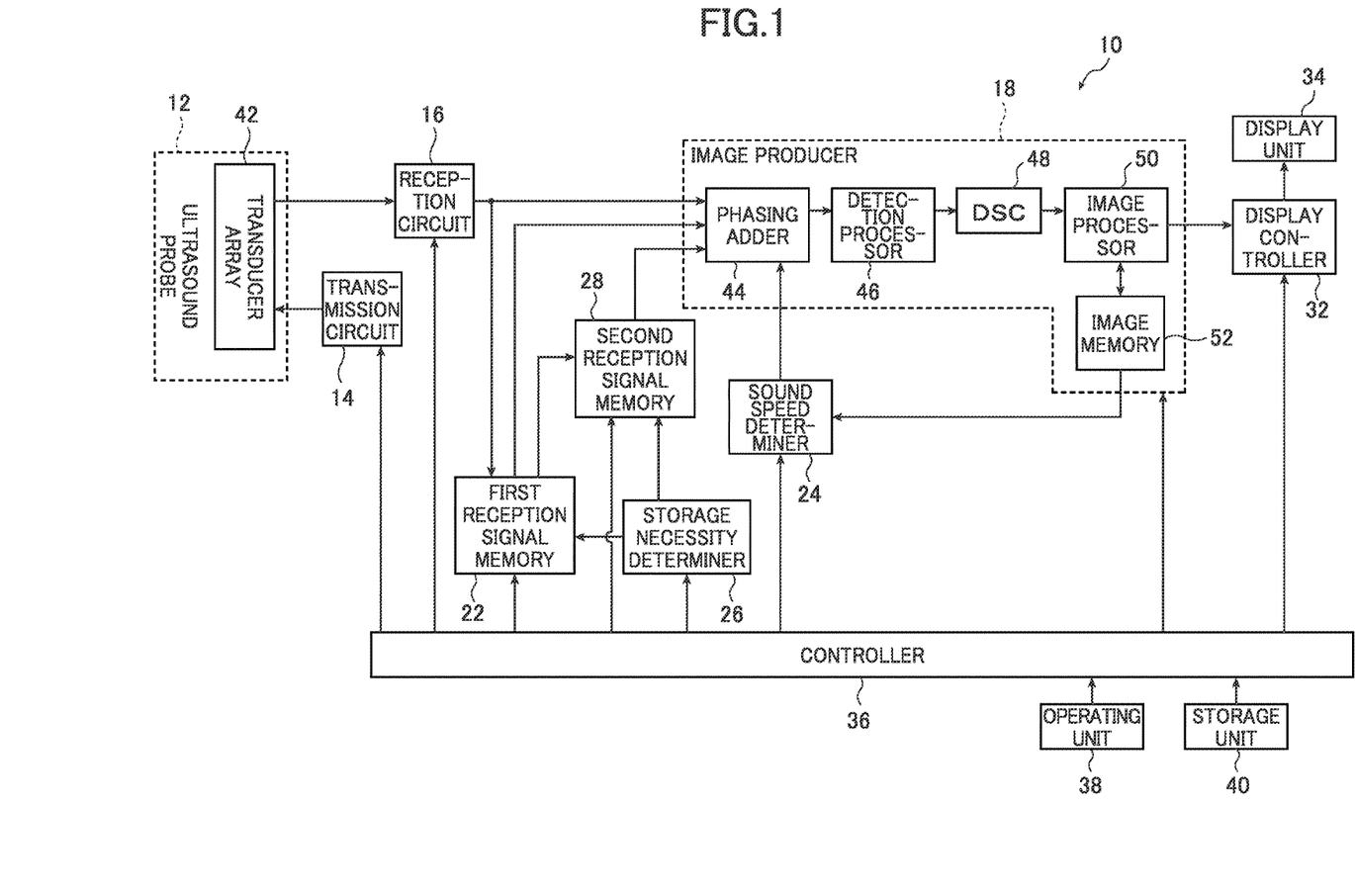
FIG. 1 is a block diagram conceptually showing the configuration of an ultrasound inspection apparatus according to the invention.

FIG. 1 shows the configuration of an ultrasound inspection apparatus according to Embodiment 1 of the invention. An ultrasound inspection apparatus 10 has an ultrasound probe 12 equipped with a transducer array 42, and a transmission circuit 14 and a reception circuit 16 are connected to the transducer array 42. A phasing adder 44, a detection processor 46, a digital scan converter (DSC) 48, and an image processor 50 of an image producer 18, a display controller 32, and a display unit 34 are sequentially connected to the reception circuit 16, and an image memory 52 is connected to the image processor 50.

A first reception signal memory 22 is connected to the reception circuit 16 and the phasing adder 44, and a sound speed determiner 24 is connected to the phasing adder 44 and the image memory 52. In addition, a storage necessity determiner 26 is connected to the first reception signal memory 22, and a second reception signal memory 28 is connected to the first reception signal memory 22, the storage necessity determiner 26, and the phasing adder 44.

Further, a controller 36 is connected to the transmission circuit 14, the reception circuit 16, the image producer 18, the display controller 32, the first reception signal memory 22, the storage necessity determiner 26, the second reception signal memory 28, and the sound speed determiner 24, and an operating unit 38 and a storage unit 40 are each connected to the controller 36.

The ultrasound probe 12 has a transducer array 42 which is used in a normal ultrasound inspection apparatus.

The transducer array 42 has a plurality of ultrasound transducers arranged in a one-dimensional or two-dimensional manner. Each ultrasound transducer transmits an ultrasonic wave according to a driving signal supplied from the transmission circuit 14 and receives an ultrasonic echo from a subject to output a reception signal. Each ultrasound transducer is constituted by a vibrator in which electrodes are formed at both ends of a piezoelectric body made of a piezoelectric ceramic represented by lead zirconate titanate (PZT), a piezoelectric polymer represented by polyvinylidene difluoride (PVDF), a piezoelectric single crystal represented by a lead magnesium niobate-lead titanate (PMN-PT) solid solution, or the like.

When a pulsed or continuous-wave voltage is applied across the electrodes of each vibrator, the piezoelectric body expands and contracts, whereby ultrasonic waves in pulsed or continuous wave form are generated from the vibrators, and an ultrasonic beam is formed by synthesizing the ultrasonic waves. When receiving the propagating ultrasonic waves, the respective vibrators expand and contract to generate electrical signals, and the electrical signals are output as the reception signals (analog element signals) of the ultrasonic waves.

The transmission circuit 14 includes, for example, a plurality of pulse generators, and adjusts the delay amount of each of driving signals for the ultrasound transducers of the transducer array 42, which serve as transmission apertures, on the basis of a transmission delay pattern selected according to a control signal from the controller 36 such that the ultrasonic waves as transmitted from the ultrasound transducers form an ultrasonic beam, then supplies the driving signals to the ultrasound transducers.

The reception circuit 16 acts according to a control signal from the controller 36 so as to amplify the signals which are output from the ultrasound transducers each serving as a reception aperture and having received an ultrasonic echo generated by the interaction between the ultrasonic beam as transmitted from the transducer array 42 and the subject, that is to say, analog element signals each from an ultrasound element and conduct analog-to-digital conversion on the amplified signals to thereby produce and output digitized element data.

Specifically, the reception circuit 16 amplifies a plurality of analog element signals received from a plurality of ultrasound elements and conducts analog-to-digital conversion on the amplified signals in response to a single transmission of an ultrasonic beam so as to produce and output one piece of digital element data including information on the ultrasound elements from which the analog element signals were received and information of reception time.

In addition, for every single transmission of the ultrasonic beam by the transmission circuit 14, the reception circuit 16 outputs one piece of element data based on the reception of ultrasonic echos. Accordingly, in response to multiple times of transmission of the ultrasonic beam for every frame by the transmission circuit 14, the reception circuit 16 outputs a plurality of pieces of element data corresponding to the respective transmissions.

The reception circuit 16 supplies the output element data to the phasing adder 44 of the image producer 18 and the first reception signal memory 22.

The first reception signal memory 22 sequentially stores element data output from the reception circuit 16. The first reception signal memory 22 associates information relating to a frame rate (for example, parameters representing the depth of the reflection position of the ultrasonic wave, the density of the scan lines, and the width of the field of vision) input from the controller 36 with the element data and stores the information.

The image producer 18 produces a sound ray signal from element data supplied from any one of the reception circuit 16, the first reception signal memory 22, and the second reception signal memory 28 under the control of the controller 36, and produces an ultrasound image from the sound ray signal.

The image producer 18 has the phasing adder 44, the detection processor 46, the DSC 48, the image processor 50, and the image memory 52.

The phasing adder 44 performs a reception focusing processing by subjecting each element signal of the element data produced by the reception circuit 16 to the corresponding delay correction according to a sound speed value set in advance or a sound speed value input from the sound speed determiner 24 described later (set sound speed and optimum sound speed) to produce delay-corrected data, and adding delay-corrected data. With this reception focusing processing, the focus of an ultrasonic echo is narrowed to produce reception data (sound ray signal).

When the element data stored in the first reception signal memory 22 is read out and a phasing and adding processing is performed thereon, the phasing adder 44 performs the reception focusing processing on the basis of an initial sound speed value set in advance. When determination of sound speed by the sound speed determiner 24 described later is performed, the phasing adder 44 reads out the element data stored in the second reception signal memory 28 and performs the reception focusing processing on the basis of a set sound speed V supplied from the sound speed determiner 24. When the element data stored in the second reception signal memory 28 is read out and the phasing and adding processing is performed thereon, the phasing adder 44 performs the reception focusing processing on the basis of an optimum sound speed supplied from the sound speed determiner 24.

This point will be described later in detail.

The phasing adder 44 supplies reception data to the detection processor 46.

The detection processor 46 corrects attenuation depending on the distance in accordance with the depth of the reflection position of the ultrasonic wave for the reception data produced by the phasing adder 44 and then performs an envelope detection processing on the reception data to produce B-mode image data which is tomographic image information relating to a tissue in the subject.

The digital scan converter (DSC) 48 subjects the B-mode image data produced by the detection processor 46 to a conversion (raster conversion) to image data based on a normal television signal scan system.

The image processor 50 performs various necessary image processings, such as a gradation processing, on the B-mode image data input from the DSC 48 to create B-mode image data available for inspection or display, and outputs the created B-mode image data for inspection or display to the display controller 32 for the sake of display or stores it in the image memory 52.

The image memory 52 temporarily stores the B-mode image data for inspection created by the image processor 50. The B-mode image data for inspection stored in the image memory 52 is read out and sent to the display controller 32 for display on the display unit 34 as necessary. Also, the B-mode image data stored in the image memory 52 is read out and sent to the sound speed determiner 24 for determination of the optimum sound speed value as necessary.

It is preferable that the image memory 52 stores all pieces of B-mode image data as imaged.

The display controller 32 causes the display unit 34 to display the ultrasound image on the basis of the B-mode image data subjected to the image processing by the image processor 50.

The display unit 34 includes, for example, a display device, such as an LCD, and displays the ultrasound image under the control of the display controller 32.

The storage necessity determiner 26 determines whether or not the element data which is temporarily stored in the first reception signal memory 22 satisfies a predetermined condition, and determines whether or not to store the element data in the second reception signal memory 28.

Specifically, in Embodiment 1, the storage necessity determiner 26 makes determination on each piece of element data on the basis of the information regarding ultrasonic transmission and reception supplied from the controller 36 so that the element data may be stored for every predetermined number of frames.

Figure 2:
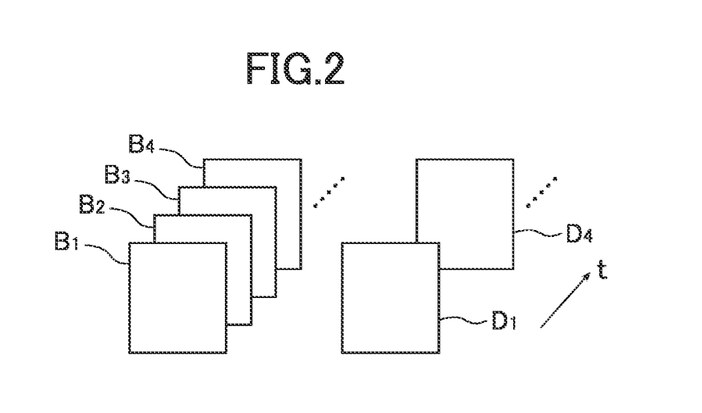
FIG. 2 is a diagram conceptually showing the result of determination by a storage necessity determiner.

FIG. 2 conceptually shows the result of determination by the storage necessity determiner 26.

In FIG. 2, $B_1$ to $B_4$ represent B-mode image data of four successive frames, respectively, and $D_1$ and $D_4$ represent element data corresponding to B-mode image data $B_1$ and $B_4$, respectively. As shown in FIG. 2, the storage necessity determiner 26 determines for every predetermined number of frames (for every three frames in the illustrated example) that the element data on one image corresponding to the frame in question is to be stored.

In the illustrated example, although the storage necessity determiner 26 is configured such that it determines that element data is to be stored for every three frames, the invention is not limited thereto, and element data may be stored for every two frames or for every four or more frames. Normally, when an operator brings the probe into contact with a region that the operator wants to observe, it is considered that the probe is caused to stand still for several seconds. Therefore, it is preferable to determine that element data is stored, for example, for every one second. Accordingly, it is preferable to determine that element data is stored at frame intervals corresponding to one second (for example, 30 frames).

The storage necessity determiner 26 supplies the result of the storage necessity determination to the first reception signal memory 22 and the second reception signal memory 28.

The second reception signal memory 28 stores element data which is determined to be stored as a result of the determination by the storage necessity determiner 26. The second reception signal memory 28 associates the element data with corresponding B-mode image data and stores the element data.

Basically, the above-described first reception signal memory 22 sequentially stores element data output from the reception circuit 16, and when the reception focusing processing of element data by the phasing adder 44 is finished, sequentially deletes the processed element data. Basically, the first reception signal memory 22 temporarily stores all pieces of element data.

In contrast, the second reception signal memory 28 continues to store only element data which is determined to be stored by the storage necessity determiner 26 even after imaging ends.

In response to the control from the controller 36, the sound speed determiner 24 provides a plurality of set sound speeds to the phasing adder 44, analyzes a plurality of pieces of B-mode image data produced by the image producer 18 using the set sound speeds and stored in the image memory 52, and for each imaged region, determines a sound speed value which gives the highest contrast or sharpness as an optimum sound speed for the relevant region.

In the invention, the optimum sound speed for a region denotes a sound speed from the ultrasound probe 12 (transducer array 42) to the region on the assumption that the space between the region and the ultrasound probe 12 is filled with a homogeneous substance. That is, the optimum sound speed is an average sound speed between the region and the ultrasound probe 12. The optimum sound speed is also referred to as an ambient sound speed.

Specifically, the sound speed determiner 24 provides a plurality of predetermined and set sound speeds V ranging from Vst to Vend with the pitches of ΔV to the phasing adder 44 in response to an instruction input from the operating unit 38 after imaging ends. Next, the sound speed determiner 24 reads out a plurality of pieces of B-mode image data from the image memory 52, which are produced on the basis of the element data read out from the second reception signal memory 28 and the respective set sound speeds V and stored in the image memory 52 by the image producer 18. The sound speed determiner 24 calculates contrast or sharpness of the read out pieces of B-mode image data for each region set in advance, and determines the set sound speed V which yields a piece of B-mode image data having the highest contrast or sharpness as the optimum sound speed for the relevant region. The sound speed determiner 24 stores the values of the optimum sound speeds determined for respective regions as a sound speed map.

Next, the sound speed determiner 24 supplies the calculated sound speed map to the phasing adder 44.

As described above, in the conventional ultrasound inspection apparatus, the optimum sound speed value is measured and sound speed correction is performed to correct distortion in an image, thereby improving image quality.

However, in the case where the sound speed value is measured during imaging of an ultrasound image, since the real-time property of display of the ultrasound image may be deteriorated, it is difficult to sufficiently improve the accuracy of the sound speed measurement.

Moreover, it has been conceived that data before image production is stored, and after imaging ends, detailed correction is performed on the stored data or data analysis is performed using the stored data. However, in the case where data is stored after phasing and adding, there is a problem in that it is not possible to correct a sound speed value used in the phasing and adding of the element data, and to perform analysis for a sound speed value, distortion or the like with high accuracy.

If element data which is a reception signal before phasing and adding is stored, it is possible to perform correction of a sound speed value used in the phasing and adding of the element data or analysis for a sound speed value, distortion or the like with high accuracy. However, since the amount of element data which is not subjected to processing such as the phasing and adding is enormous, such element data is only temporarily stored, and the element data after being subjected to processing such as the phasing and adding is sequentially deleted.

In contrast, according to the invention, the necessity for storage of element data is determined on the basis of a predetermined condition, and element data which satisfies the predetermined condition is stored. Accordingly, it is possible to prevent an increase in the amount of data to be stored, and to prevent real-time property of display of an ultrasound image from being deteriorated during ultrasound imaging without increasing a load due to sound speed calculation or the like. In addition, after the imaging ends, it is possible to perform calculation of the sound speed value or analysis for distortion or the like with high accuracy using the stored element data and thus to improve image quality, and to perform tissue characterization or the like with high accuracy.

The set sound speeds V may be sought on condition that the value Vst is 1400 m/s, the value Vend is 1700 m/s, and the pitch ΔV is about 10 to 50 m/s.

The sound speed determiner 24 is adapted to divide an image into a plurality of predetermined areas and determine the optimum sound speed for each area, although the invention is not limited thereto. The optimum sound speed may be determined for the entire image without dividing the image into a plurality of areas.

The controller 36 controls various components of the ultrasound inspection apparatus on the basis of instructions input from the operating unit 38 by the operator.

When the operator inputs various kinds of information through the operating unit 38, in particular, inputs information necessary for the determination by the storage necessity determiner 26 whether or not to store element data and information necessary for the determination of the optimum sound speed value by the sound speed determiner 24, the controller 36 supplies the information input from the operating unit 38 to such components as the transmission circuit 14, the reception circuit 16, the image producer 18, the first reception signal memory 22, the sound speed determiner 24, the storage necessity determiner 26, and the second reception signal memory 28 as necessary.

The operating unit 38 is used when the operator performs an input operation, and can be formed of a keyboard, a mouse, a trackball, a touch panel, or the like.

The storage unit 40 stores various kinds of information input from the operating unit 38, information necessary for processings or operations performed by various components under the control of the controller 36, operating programs for causing various components to execute processings or operations, and the like, and as the storage unit 40, a recording medium such as a hard disk, a flexible disk, an MO, an MT, a RAM, a CD-ROM, a DVD-ROM, an SD card, a CF card and a USB memory or a server may be used.

Although the phasing adder 44, the detection processor 46, the DSC 48, the image processor 50, the display controller 32, the storage necessity determiner 26, and the sound speed determiner 24 are constituted by a CPU and operating programs for causing the CPU to perform various processings, these components may be constituted by digital circuits.

Next, the operation of Embodiment 1 will be described.

If the operator brings the ultrasound probe 12 into contact with the surface of the subject and starts a measurement, the ultrasonic waves are transmitted from the ultrasound transducers of the transducer array 42 in accordance with the driving signals supplied from the transmission circuit 14. An analog element signal is output from each ultrasound transducer, which receives an ultrasonic echo from the subject, to the reception circuit 16. Element data is produced by the reception circuit 16 and stored in the first reception signal memory 22. Ultrasonic transmission and reception are repeated by switching between transmission apertures and reception apertures, and a plurality of pieces of element data produced are stored in the first reception signal memory 22.

The storage necessity determiner 26 determines the necessity for storage of the element data temporarily stored in the first reception signal memory 22 on the basis of information relating to the frame rate of the element data such that the element data is stored in the second reception signal memory 28 for every predetermined number of frames.

The second reception signal memory 28 stores the element data which is determined to be stored as a result of the determination by the storage necessity determiner 26.

The phasing adder 44 of the image producer 18 receives element data output from the reception circuit 16 or reads out the element data as temporarily stored in the first reception signal memory 22. The phasing adder 44 performs the delay correction on the element data on the basis of the sound speed value set in advance (initial sound speed value) and adds element data to produce the sound ray signal. The detection processor 46 of the image producer 18 performs the attenuation correction and the envelope detection processing on the sound ray signal to produce B-mode image data.

The B-mode image data is subjected to raster conversion by the DSC 48, then to various image processings by the image processor 50, supplied to the display controller 32, and used for display on the display unit 34. Accordingly, the ultrasound image is displayed on the display unit 34 in real time. The B-mode image data is stored in the image memory 52.

Next, the operation of the ultrasound inspection apparatus 10 when sound speed correction is performed after imaging ends will be described.

B-mode image data which is subjected to the sound speed correction is selected from B-mode image data stored in the image memory 52 in response to an input from the operating unit 38. The phasing adder 44 of the image producer 18 reads out element data corresponding to the selected B-mode image data from the second reception signal memory 28. The phasing adder 44 performs the reception focusing processing on the element data on the basis of the predetermined and set sound speed V supplied from the sound speed determiner 24 to produce the sound ray signal. The image producer 18 produces B-mode image data from the sound ray signal and stores the B-mode image data in the image memory 52. The image producer 18 produces a plurality of pieces of B-mode image data on the basis of a plurality of set sound speeds V, respectively, and stores the pieces of B-mode image data in the image memory 52.

The sound speed determiner 24 calculates contrast or sharpness of a plurality of pieces of B-mode image data produced on the basis of a plurality of set sound speeds V for each predetermined region, determines a set sound speed V which gives the highest contrast or sharpness as the optimum sound speed for the relevant region, stores information regarding the optimum sound speeds for the respective regions as a sound speed map, and supplies the sound speed map to the phasing adder 44.

The phasing adder 44 performs the reception focusing processing on element data, which is read out from the second reception signal memory 28 and which corresponds to the selected B-mode image data, on the basis of the optimum sound speed supplied from the sound speed determiner 24 to produce the sound ray signal. The image producer 18 produces new B-mode image data from the sound ray signal and supplies the new B-mode image data to the display controller 32 and the image memory 52.

The display controller 32 supplies the new B-mode image data to the display unit 34.

In this way, according to the invention, since the necessity for storage of element data is determined on the basis of a predetermined condition, and element data which satisfies the predetermined condition is stored, it is possible to prevent an increase in the amount of data to be stored. In addition, during imaging of the ultrasound image, it is possible to prevent real-time property of display of the ultrasound image from being deteriorated, and after the imaging ends, it is possible to calculate the optimum sound speed using the stored element data and re-produce an image on the basis of the optimum sound speed, thereby improving image quality.

Moreover, since element data is stored in the second reception signal memory 28, in addition to correcting the sound speed value to re-produce an image, tissue characterization may be performed on the basis of the stored element data.

Alternatively, by using the element data stored in the second reception signal memory 28, a plurality of pieces of element data may be corrected in time and position on the basis of information regarding the reception time and information regarding geometric arrangement of the respective elements of the transducer array 42, and then the corrected pieces of element data may be superimposed on one another to reconstruct element data. By superimposing a plurality of pieces of element data on one another to reconstruct element data, it is possible to improve signal quality, and image quality accordingly.

While, in Embodiment 1 described above, the phasing adder 44 performs the reception focusing processing during imaging of the ultrasound image on the basis of the initial sound speed value set in advance, the invention is not limited thereto, and the reception focusing processing may be performed using the optimum sound speed calculated just before the reception focusing processing.

In Embodiment 1, the sound speed determiner 24 does not determine the optimum sound speed during imaging of the ultrasound image but determines the optimum sound speed in response to an instruction input from the operating unit 38 after the imaging ends. The invention, however, is not limited to such configuration, and the sound speed determiner 24 may determine the optimum sound speed also during the imaging and determine a more detailed optimum sound speed after the imaging ends.

Specifically, for example, the determination of the optimum sound speed may be performed when imaging starts, and an image may be produced on the basis of the optimum sound speed during imaging. Alternatively, the determination of the optimum sound speed during imaging may be performed for every several frames, element data may be stored in the second reception signal memory 28 at frame intervals shorter than those at which the determination of the optimum sound speed is performed, and after imaging ends, the determination of the optimum sound speed may be performed using the stored element data. Alternatively, the determination of the optimum sound speed during imaging may be performed for each of subregions defined by roughly dividing the region to be imaged, and the determination of the optimum sound speed after imaging may be performed for each of smaller subregions.

Alternatively, the sound speed determiner 24 may calculate the optimum sound speed for each region during imaging and calculate a local sound speed value for each region after imaging ends.

Here, the local sound speed value refers to a local sound speed value at a position of each region in the subject. The calculation of the local sound speed value may be performed by, for example, a method described in JP 2010-99452 A owned by FUJIFILM Corporation.

Figure 3:
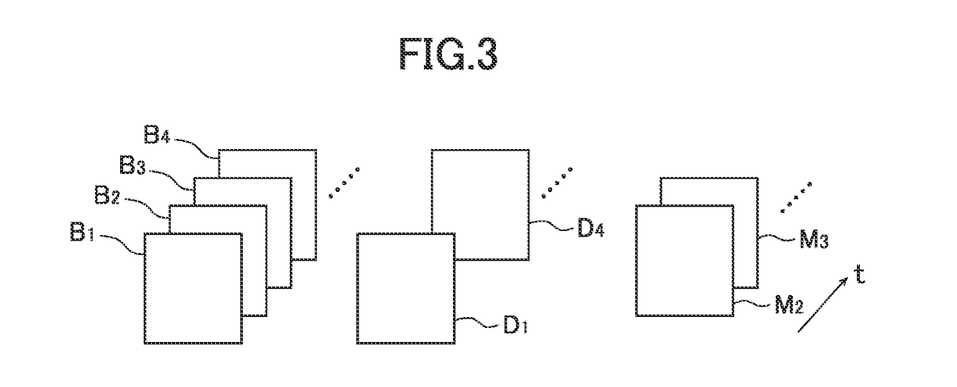
FIG. 3 is a diagram conceptually showing another example of data to be stored.

In Embodiment 1, the second reception signal memory 28 is adapted to store element data at predetermined frame intervals. In addition to this, as shown in FIG. 3, the second reception signal memory 28 may store the optimum sound speed calculated during imaging with the frame whose element data is not stored. In FIG. 3, $B_1$ to $B_4$ represent B-mode image data of four successive frames, respectively, $D_1$ and $D_4$ represent element data corresponding to B-mode image data $B_1$ and $B_4$, respectively, and $M_2$ and $M_3$ represent the optimum sound speeds (sound speed map) corresponding to B-mode image data $B_2$ and $B_3$, respectively.

While the storage necessity determiner 26 in Embodiment 1 is adapted to determine whether or not to store element data at predetermined frame intervals, the invention is not limited thereto, and the determination may be made on the basis of whether or not element data corresponds to a predetermined region in an image.

Figure 4:
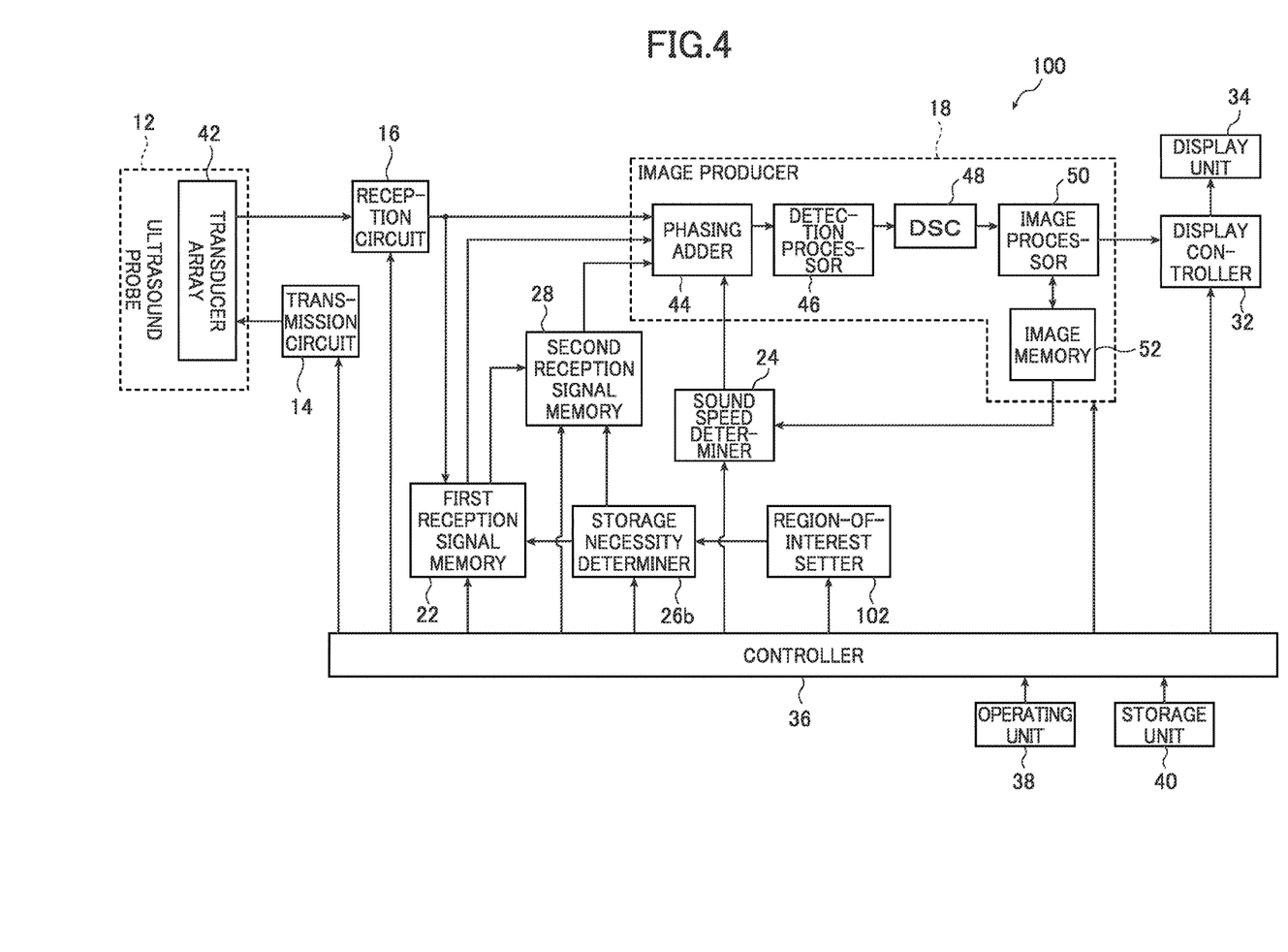
FIG. 4 is a block diagram conceptually showing the configuration of another example of an ultrasound inspection apparatus according to the invention.

FIG. 4 shows the configuration of an ultrasound inspection apparatus 100 according to Embodiment 2 of the invention.

The ultrasound inspection apparatus 100 shown in FIG. 4 has the same configuration as the ultrasound inspection apparatus 10 shown in FIG. 1, except that a storage necessity determiner 26b is provided instead of the storage necessity determiner 26, and a region-of-interest setter 102 is provided. Accordingly, the same constituents are denoted by the same reference numerals, and detailed description thereon will not be repeated.

The ultrasound inspection apparatus 100 has an ultrasound probe 12, a transmission circuit 14 and a reception circuit 16 both connected to the ultrasound probe 12, an image producer 18, a first reception signal memory 22, a sound speed determiner 24, the storage necessity determiner 26b, a second reception signal memory 28, a display controller 32, a display unit 34, a controller 36, an operating unit 38, a storage unit 40, and the region-of-interest setter 102.

The region-of-interest setter 102 sets a region of interest ROI in response to an input from the operating unit 38 by the operator.

Figure 5:
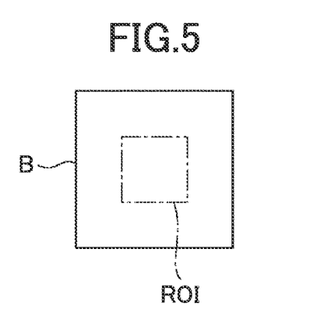
FIG. 5 is a diagram conceptually showing an image in which a region of interest is set.

FIG. 5 is a diagram schematically showing an example of an ultrasound image B in which a region of interest ROI is set.

The region of interest ROI can be arbitrarily set by the operator, and the region of interest ROI is so set as to include a target region to be observed, such as a tissue (organ) or a lesion.

The region-of-interest setter 102 supplies information regarding the set region of interest ROI to the storage necessity determiner 26b.

The region-of-interest setter 102 is not limited to one having a configuration in which the region of interest ROI is set in response to an input from the operating unit 38, and the region-of-interest setter 102 may have a configuration in which the ultrasound image (B-mode image data) produced by the image producer 18 is analyzed to set the region of interest ROI.

For example, the region-of-interest setter 102 may extract a structural region on the basis of the difference in luminance value between adjacent pixels in the ultrasound image produced by the image producer 18. Specifically, the position (pixels) where the difference in luminance value between adjacent pixels is equal to or greater than a predetermined value may be determined as a margin (edge) of the structural region (tissue or lesion), a region which is surrounded by such edges or a region which includes many such edges may be determined as the structural region, namely, the target region and extracted, and a region which includes the target region and has predetermined shape and size may be set as the region of interest ROI.

The storage necessity determiner 26b determines whether or not to store element data in the second reception signal memory 28 on the basis of information regarding the region of interest ROI set by the region-of-interest setter 102.

Figure 6A:
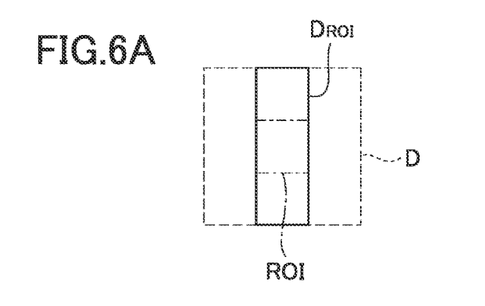
FIGS. 6A to 6C are diagrams conceptually showing element data which is stored in the ultrasound inspection apparatus shown in FIG. 4.

Specifically, as shown in FIG. 6A, element data of a plurality of lines corresponding to the region of interest ROI is determined as element data $D_{ROI}$ to be stored among element data D stored in the first reception signal memory 22.

The second reception signal memory 28 stores the element data $D_{ROI}$ of the lines corresponding to the region of interest ROI on the basis of the determination result of the storage necessity determiner 26b.

After imaging ends, the sound speed determiner 24 analyzes a plurality of pieces of B-mode image data of the region of interest ROI which are respectively produced by the image producer 18 on the basis of a plurality of set sound speeds V using the element data $D_{ROI}$ corresponding to the region of interest ROI that is stored in the second reception signal memory 28, and determines a sound speed value which gives the highest image contrast or sharpness as the optimum sound speed for the region of interest ROI.

The sound speed determiner 24 supplies the calculated optimum sound speed to the image producer 18.

The image producer 18 produces new B-mode image data of the region of interest ROI from the element data $D_{ROI}$ corresponding to the region of interest ROI that is stored in the second reception signal memory 28 on the basis of the optimum sound speed. Further, out of the B-mode image data in the same frame that is stored in the image memory 52, the image data of the region of interest is substituted with the new B-mode image data to reconstruct the B-mode image data.

The image producer 18 supplies the reconstructed B-mode image data to the display controller 32, and a B-mode image on the basis of the reconstructed B-mode image data is displayed on the display unit 34.

In this way, since only element data $D_{ROI}$ of lines corresponding to the region of interest ROI is stored, it is possible to prevent an increase in the amount of data to be stored. During imaging of the ultrasound image, it is possible to prevent real-time property of display of the ultrasound image from being deteriorated. After imaging ends, the optimum sound speed is calculated using the stored element data of the region of interest ROI, and the image of the region of interest ROI is re-produced on the basis of the optimum sound speed, thereby improving image quality of the region of interest ROI.

In addition, for the region of interest ROI, tissue characterization or the like may be performed using the stored element data.

Figure 6B:
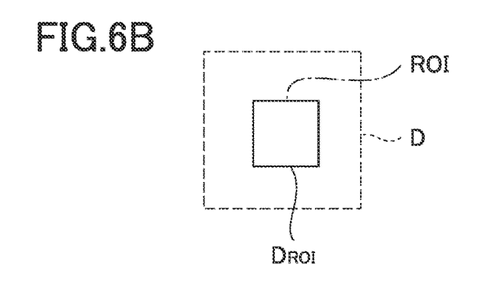
Figure 6C:
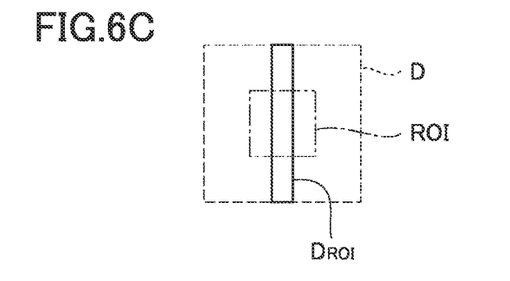

In Embodiment 2 described above, the storage necessity determiner 26b determines element signals of lines corresponding to the region of interest ROI as element data $D_{ROI}$ to be stored, to which the invention is not limited. As shown in FIG. 6B, element data at a position corresponding to the region of interest ROI may be determined as element data $D_{ROI}$ to be stored. Alternatively, as shown in FIG. 6C, element data of the central line of the region of interest ROI and several adjacent lines may be determined as element data $D_{ROI}$ to be stored. In that case, the element data $D_{ROI}$ may be element data of lines whose number allows the calculation of the optimum sound speed for the region of interest ROI.

In Embodiment 2, the sound speed determiner 24 determines the optimum sound speed value for the region of interest ROI as a single region, although the invention is not limited thereto. The region of interest ROI may be divided into a plurality of subregions and the optimum sound speed value may be determined for each subregion.

In Embodiment 2, element data corresponding to the region of interest ROI is stored in every frame, although the invention is not limited thereto, and element data corresponding to the region of interest ROI may be stored at predetermined frame intervals.

In Embodiment 2 described above, the storage necessity determiner 26b determines to store element data corresponding to the region of interest ROI, to which the invention is not limited. The storage necessity determiner 26b may determine to store element data corresponding to a predetermined region, for example, element data corresponding to a region at the depth of visual field as designated by a depth button.

In Embodiment 1 described above, determination of whether or not to store element data is made at predetermined frame intervals, to which the invention is not limited. Determination of whether or not to store element data may be made at a predetermined timing.

In an ultrasound inspection apparatus having a region-of-interest setter according to Embodiment 3 of the invention, a storage necessity determiner determines to store element data of subsequent frames after the region of interest ROI is set or after an operation to set the region of interest ROI is detected.

In Embodiment 3, the storage necessity determiner may determine to store all pieces of element data of subsequent frames after the region of interest ROI is set, or may determine to store element data for a predetermined number of frames after the region of interest ROI is set.

Moreover, the storage necessity determiner may determine to store element data of the entire image of a frame after the region of interest ROI is set, or may determine to store element data corresponding to the region of interest ROI after the region of interest ROI is set.

In Embodiment 1, the storage necessity determiner 26 determines whether or not to store element data at predetermined frame intervals, although the invention is not limited thereto, and the determination may be made on the basis of the operation of the probe.

Figure 7:
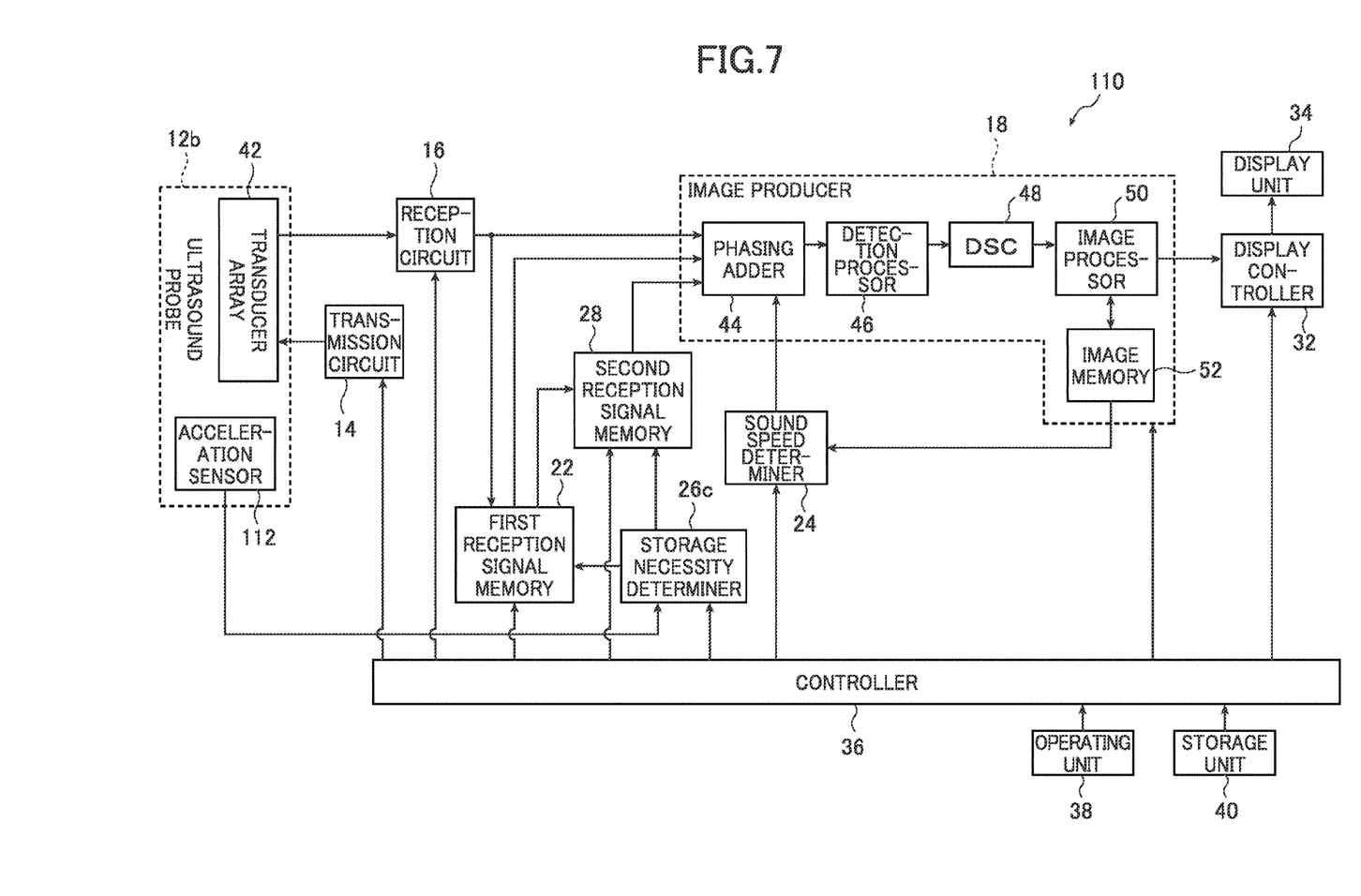
FIG. 7 is a block diagram conceptually showing the configuration of yet another example of an ultrasound inspection apparatus according to the invention.

FIG. 7 shows the configuration of an ultrasound inspection apparatus 110 according to Embodiment 4 of the invention.

The ultrasound inspection apparatus 110 shown in FIG. 7 has the same configuration as the ultrasound inspection apparatus 10 shown in FIG. 1, except that a storage necessity determiner 26c is provided instead of the storage necessity determiner 26, and an ultrasound probe 12b having an acceleration sensor 112 is provided instead of the ultrasound probe 12. Accordingly, the same constituents are denoted by the same reference numerals, and detailed description thereof will not be repeated.

The ultrasound inspection apparatus 110 has the ultrasound probe 12b, a transmission circuit 14 and a reception circuit 16 both connected to the ultrasound probe 12b, an image producer 18, a first reception signal memory 22, a sound speed determiner 24, a storage necessity determiner 26c, a second reception signal memory 28, a display controller 32, a display unit 34, a controller 36, an operating unit 38, and a storage unit 40.

The ultrasound probe 12b has a transducer array 42 and the acceleration sensor 112.

The acceleration sensor 112 is a sensor which measures acceleration to detect movement of the ultrasound probe 12b, and various known acceleration sensors, such as a piezoresistance type acceleration sensor and a capacitance type acceleration sensor, may be used.

The acceleration sensor 112 supplies information regarding the detected acceleration to the storage necessity determiner 26c.

The storage necessity determiner 26c determines from the information on acceleration as supplied from the acceleration sensor 112 to store element data if the acceleration in question is equal to or less than a predetermined threshold value. That is, the storage necessity determiner 26c determines to store element data acquired when the ultrasound probe 12b stands still.

According to the determination by the storage necessity determiner 26c, the second reception signal memory 28 stores element data acquired when the ultrasound probe 12b is not moved.

During imaging of the ultrasound image, the operator appropriately moves the ultrasound probe 12b to search for a region of interest in the subject. For this reason, during imaging, the ultrasound probe 12b may repeatedly be caused to move and stand still. Element data during movement of the ultrasound probe 12b cannot be said to be accurate data, and it is not possible to perform sufficient improvement of image quality with such element data. In addition, an ultrasound image obtained when the ultrasound probe 12b is not moved appears to be an image that the operator wants to observe.

For this reason, as in Embodiment 4, the storage necessity determiner 26c determines to store element data acquired when the ultrasound probe 12b is not moved, thereby preventing storage of unnecessary element data and thus preventing an increase in the amount of data to be stored. During imaging of the ultrasound image, it is possible to prevent real-time property of display of the ultrasound image from being deteriorated, and after imaging ends, the optimum sound speed is calculated using the stored element data and an image is re-produced on the basis of the optimum sound speed, thereby improving image quality.

The storage necessity determiner 26c may determine to store all pieces of element data while it is considered that the ultrasound probe 12b is not moved, or may determine to store element data for a predetermined number of frames while it is considered that the ultrasound probe 12b is not moved.

Alternatively, the storage necessity determiner 26c may determine to store all pieces of element data while it is considered that the ultrasound probe 12b is not moved, and determine to store element data for a predetermined number of frames while it is considered that the ultrasound probe 12b is moved.

In the case where the region of interest ROI is set, the storage necessity determiner 26c may determine to store element data corresponding to the region of interest ROI while it is considered that the ultrasound probe 12b is not moved.

In Embodiment 4 described above, the acceleration sensor 112 is provided in the ultrasound probe 12b to detect movement and standstill of the ultrasound probe 12b, to which the invention is not limited. The movement and standstill of the ultrasound probe 12b may be detected from the amount of change in B-mode image data between successive frames. Specifically, the difference in luminance value between the B-mode image data as just imaged and the B-mode image data of the previous frame is found, and when the difference is equal to or smaller than a predetermined threshold value, it is considered that the ultrasound probe 12b stands still.

A determination method in the storage necessity determiner is not limited to the configurations of Embodiments 1 to 4 described above, and it may be determined to store element data when the image mode is specified (to any one of B mode, compound mode, and harmonic mode).

By storing element data when the image mode is specified, element data can be used to improve image quality in the specified image mode.

Alternatively, a determination method in the storage necessity determiner may be configured such that element data obtained by receiving an ultrasonic echo of an ultrasonic beam transmitted at a predetermined transmit frequency is stored.

If element data obtained by ultrasonic transmission and reception at a predetermined transmit frequency is stored, for example, at the time of transmission at a low frequency, an ultrasonic echo from a deep portion can be received, thereby improving image quality for the deep portion.

Alternatively, a determination method in the storage necessity determiner may be configured such that element data obtained by receiving an ultrasonic echo of an ultrasonic beam transmitted with a predetermined amplitude (power) is stored.

If element data obtained by ultrasonic transmission and reception with a predetermined amplitude is stored, for example, at the time of transmission with high output power, an ultrasonic echo from a deep portion can be received, thereby improving image quality f the deep portion.

A signal processing program is not limited to one being stored in a memory attached to the controller. The signal processing program may be recorded in a memory medium (removable medium), such as a CD-ROM, which is removably loaded in the ultrasound inspection apparatus and may be read into the apparatus through an interface corresponding to the removable medium.

While the ultrasound inspection apparatus, the signal processing method for an ultrasound inspection apparatus, and the recording medium of the present invention have been described in detail, the present invention is not limited to the above embodiments but may be improved or modified in various forms without departing from the gist of the present invention.

What is claimed is:

1. An ultrasound inspection apparatus which inspects an inspection object using an ultrasonic beam, the ultrasound inspection apparatus comprising:
   a transducer array having elements arranged therein that transmits the ultrasonic beam and receives an ultrasonic echo reflected by the inspection object to output an element signal according to the ultrasonic echo as received;
   a transmitter adapted to cause the transducer array to transmit the ultrasonic beam with the two or more elements serving as transmission apertures;
   a receptor adapted to perform analog-to-digital conversion on two or more element signals which are output from the transducer array having received ultrasonic echos with the two or more elements serving as reception apertures, so as to output resulting signals as one piece of element data;
   a first reception signal memory which stores a plurality of pieces of element data output from the receptor as a result of repeating ultrasonic transmission and reception through the transmitter and the receptor multiple times;
   an image producer adapted to perform phasing and adding individually on one or more pieces of element data based on a specified sound speed value to produce one or more sound ray signals, and produce ultrasound image data from the one or more sound ray signals;
   a sound speed determiner adapted to determine an optimum sound speed value from a plurality of pieces of ultrasound image data which are individually produced by the image producer based on a plurality of specified and set sound speeds and using one or more pieces of element data;
   a storage necessity determiner adapted to determine each piece of element data stored in the first reception signal memory whether or not to satisfy a specified condition; and
   a second reception signal memory which stores a piece of element data determined by the storage necessity determiner to satisfy the specified condition,
   wherein the image producer, the sound speed determiner, and the storage necessity determiner are composed of a central processing unit and an operation program or a digital circuit;
   the piece of element data which is stored in the second reception signal memory is data which has not been subjected to phasing and adding;
   during imaging, the storage necessity determiner determines whether the element data satisfies the predetermined condition, and the second reception signal memory stores the element data which is determined to satisfy the predetermined condition;
   after imaging ends, the sound speed determiner determines the optimum sound speed value, and the image producer produces ultrasound image data using the element data which is stored in the second reception signal memory based on the optimum sound speed value.

2. The ultrasound inspection apparatus according to claim 1, further comprising a region-of-interest setter adapted to set a region of interest in an imaging region,
   wherein the storage necessity determiner determines a piece of element data corresponding to the region of interest to satisfy the specified condition.

3. A signal processing method for an ultrasound inspection apparatus provided with a transducer array having elements arranged therein that transmits an ultrasonic beam and receives an ultrasonic echo reflected inside an inspection object to output an element signal according to the ultrasonic echo as received, which apparatus generates an ultrasonic beam by the transducer array to inspect the inspection object and produce ultrasound image data, the signal processing method comprising:

a transmission step of causing the transducer array to transmit the ultrasonic beam with the two or more elements serving as transmission apertures;

a reception step of performing analog-to-digital conversion on two or more element signals which are output from the transducer array having received ultrasonic echos with the two or more elements serving as reception apertures, so as to output resulting signals as one piece of element data;

a first signal storage step of storing a plurality of pieces of element data output in the reception step as a result of repeating the transmission step and the reception step multiple times;

an image production step of performing phasing and adding individually on one or more pieces of element data based on a specified sound speed value to produce one or more sound ray signals, and producing ultrasound image data from the one or more sound ray signals;

a sound speed determination step of determining an optimum sound speed value from a plurality of pieces of ultrasound image data which are individually produced in the image production step based on a plurality of specified and set sound speeds and using one or more pieces of element data;

a storage necessity determination step of determining each piece of element data stored in the first signal storage step whether or not to satisfy a specified condition; and a second signal storage step of storing a piece of element data determined in the storage necessity determination step to satisfy the specified condition, wherein the piece of element data which is stored in the second signal storage step is data which has not been subjected to phasing and adding;

during imaging, in the storage necessity determination step, it is determined whether the element data satisfies the predetermined condition, and in the second signal storage step, the element data which is determined to satisfy the predetermined condition is stored; and after imaging ends, in the sound speed determination step, the optimum sound speed value is determined, and in the image production step, ultrasound image data is produced using the element data which is stored in the second reception signal memory based on the optimum sound speed value.

4. A computer-readable non-transitory recording medium having a signal processing program for an ultrasound inspection apparatus recorded thereon, wherein the signal processing program causes a computer to execute a signal processing method for an ultrasound inspection apparatus provided with a transducer array having elements arranged therein that transmits an ultrasonic beam and receives an ultrasonic echo reflected inside an inspection object to output an element signal according to the ultrasonic echo as received, which apparatus generates an ultrasonic beam by the transducer array to inspect the inspection object and produce ultrasound image data, the signal processing method comprising:

a transmission step of causing the transducer array to transmit the ultrasonic beam with the two or more elements serving as transmission apertures;

a reception step of performing analog-to-digital conversion on two or more element signals which are output from the transducer array having received ultrasonic echos with the two or more elements serving as reception apertures, so as to output resulting signals as one piece of element data;

a first signal storage step of storing a plurality of pieces of element data output in the reception step as a result of repeating the transmission step and the reception step multiple times;

an image production step of performing phasing and adding individually on one or more pieces of element data based on a specified sound speed value to produce one or more sound ray signals, and producing ultrasound image data from the one or more sound ray signals;

a sound speed determination step of determining an optimum sound speed value from a plurality of pieces of ultrasound image data which are individually produced in the image production step based on a plurality of specified and set sound speeds and using one or more pieces of element data;

a storage necessity determination step of determining each piece of element data stored in the first signal storage step whether or not to satisfy a specified condition; and a second signal storage step of storing a piece of element data determined in the storage necessity determination step to satisfy the specified condition, wherein the piece of element data which is stored in the second signal storage step is data which has not been subjected to phasing and adding;

during imaging, in the storage necessity determination step, it is determined whether the element data satisfies the predetermined condition, and in the second signal storage step, the element data which is determined to satisfy the predetermined condition is stored; and after imaging ends, in the sound speed determination step, the optimum sound speed value is determined, and in the image production step, ultrasound image data is produced using the element data which is stored in the second reception signal memory based on the optimum sound speed value.

5. The ultrasound inspection apparatus according to claim 1, wherein:

the sound speed determiner determines the optimum sound speed value from a plurality of pieces of ultrasound image data which are individually produced by the image producer based on a plurality of specified and set sound speeds and using the one or more pieces of element data stored in the second reception signal memory; and the image producer produces ultrasound image data based on an initial sound speed value set in advance when producing ultrasound image data from the plurality of pieces of element data stored in the first reception signal memory, and produces ultrasound image data based on the optimum sound speed value calculated by the sound speed determiner when producing ultrasound image data from the one or more pieces of element data stored in the second reception signal memory.

6. The ultrasound inspection apparatus according to claim 1, wherein the second reception signal memory associates the piece of element data determined by the storage necessity determiner to satisfy the specified condition with a piece of ultrasound image data corresponding to the piece of element data so as to store them as such.

7. The ultrasound inspection apparatus according to claim 1, further comprising an image memory which stores ultrasound image data produced by the image producer, wherein:
the image memory stores ultrasound image data of all frames; and
the second reception signal memory stores pieces of element data at specified frame intervals.

8. The ultrasound inspection apparatus according to claim 1, further comprising a region-of-interest setter adapted to set a region of interest in an imaging region,
wherein, when an operation to set the region of interest has been detected, the storage necessity determiner determines pieces of element data corresponding to subsequent frames to satisfy the specified condition.

9. The ultrasound inspection apparatus according to claim 1, further comprising a movement detector adapted to detect movement and standstill of a probe equipped with the transducer array,
wherein, when the movement detector has detected standstill, of the probe, the storage necessity determiner determines a piece of element data of a frame corresponding to the standstill of the probe to satisfy the specified condition.

10. The ultrasound inspection apparatus according to claim 1, wherein, when a specified mode has been selected, the storage necessity determiner determines pieces of element data corresponding to subsequent frames to satisfy the specified condition.

11. The ultrasound inspection apparatus according to claim 1, wherein the storage necessity determiner determines a piece of element data which is obtained by transmitting an ultrasonic beam at a specified transmit frequency to satisfy the specified condition.

12. The ultrasound inspection apparatus according to claim 1, wherein the storage necessity determiner determines a piece of element data which is obtained by transmitting an ultrasonic beam having a specified amplitude to satisfy the specified condition.

13. The ultrasound inspection apparatus according to claim 1, further comprising an image memory which stores ultrasound image data produced by the image producer, wherein:
the sound speed determiner determines the optimum sound speed value from a plurality of pieces of ultrasound image data which are individually produced by the image producer based on a plurality of specified and set sound speeds and using the pieces of element data stored in the first reception signal memory;
the image memory stores ultrasound image data of all frames; and
the second reception signal memory stores pieces of element data at specified frame intervals, and stores the optimum sound speed value for a frame whose element data is not stored.

* * * * *